(12) United States Patent
Dhugga et al.

(10) Patent No.: US 6,706,951 B1
(45) Date of Patent: Mar. 16, 2004

(54) MAIZE NUCLEIC ACID ENCODING A GDP-MANNOSE PYROPHOSPHORYLASE

(75) Inventors: Kanwarpal S. Dhugga, Johnston, IA (US); Xun Wang, San Diego, CA (US); Benjamin A. Bowen, Berkeley, CA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/374,967

(22) Filed: Aug. 16, 1999

Related U.S. Application Data

(60) Provisional application No. 60/096,782, filed on Aug. 17, 1998.

(51) Int. Cl.[7] .......................... A01H 5/00; C12N 15/82; C12N 15/54
(52) U.S. Cl. ................. 800/298; 536/23.2; 435/419
(58) Field of Search .................. 435/6, 468, 410, 435/419, 320.1, 430; 536/23.1, 24.1, 24.5; 800/278, 286, 287, 289, 284, 298, 312, 306, 322, 320.1, 320.2, 320, 320.3

(56) References Cited

U.S. PATENT DOCUMENTS

| | | | | |
|---|---|---|---|---|
| 4,363,669 A | * | 12/1982 | Cottrell et al. | 106/205 |
| 5,194,596 A | * | 3/1993 | Tischer | 530/399 |
| 5,350,836 A | * | 9/1994 | Kopchick et al. | 530/399 |

FOREIGN PATENT DOCUMENTS

| | | |
|---|---|---|
| CA | 2214458 | 9/1996 |
| EP | 0380470 B1 | 2/1995 |

OTHER PUBLICATIONS

Hashimoto et al, 1997, J. Biol. Chem. 272:16308–16314.*
Wheeler et al, 1998, Nature 393:365–369.*
Colliver et al, 1997, Plant Mol. Biol. 35:509–522.*
Lazar et al, 1988, Mol. Cell. Biol. 8:1247–1252.*
Hill et al, 1998, Biochem. Biophys. Res. Comm. 244:573–577.*
Gordon–Kamm et al, 1990, Plant Cell 2:603–618.*
Facciotti et al, 1985, BioTechnology 3:241–246.*
Vincenzo De Luca, Molecular characterization of secondary metabolic pathways, AGBIOTECH News and Information 1993 vol. 5, No. 6, pp. 225N–229N.*
Gregory Stephanopoulos et al., Metabolic engineering—methodologies and future prospects, TIBTECH Sep. 1993 (vol. 11), pp. 392–396.*
Genetwork, TIG Oct. 1996 vol. 12, No. 10, pp. 425–427.*
Errors in genome annotation, TIG Apr. 1999, vol. 15, No. 4, pp. 132–133.*
Temple F. Smith et al., The challenges of genome sequence annotation or "The devil is in the details", Nature Biotechnology, vol. 15, Nov. 1997, pp. 1222–1223.*
C.C.Pilbeam et al., Comparison of the Effects of Various Lengths of Synthetic Human Parathyroid Hormone–Related Peptide (hPTHrP) of Malignancy on Bone Resorption and Formation in Organ Culture, BONE, 14, pp. 717–720.*
Slobodan Vukicevic et al., Induction of nephrogenic mesenchyme by osteogenic protein 1 (bone morphogenetic protein 7), Proc. Natl. Acad. Sci. USA, vol. 93, pp. 9021–9026.*
Laura E. Benjamin et al., A plasticity window for blood vessel remodeling is defined by pericyte coverage of the preformed endothelial network and is regulated by PDGF–B and VEGF, DEVELOPMENT 125, pp. 1591–1598.*
Genetwork, Protein annotation: detective work for function prediction, TIG Jun. 1998 vol. 14, No. 6, pp. 248–250.*
Jeffrey Skolnick et al., From genes to protein structure and function: novel applications of computational approaches in the genomic era, Trends in Biotech, 18 (1): pp. 34–39.*
Peer Bork, Powers and Pitfalls in Sequence Analysis: The 70% Hurdle, Genome Research, pp. 398–400.*
James A. Wells, Additivity of Mutational Effects in Proteins, BIOCHEMISTRY, vol. 29, No. 37, Sep. 18, 1990, pp. 8509–8517.*
J. Thomas Ngo et al., Computational Complexity, Protein Structure Prediction, and the Levinthal Paradox, pp. 491–495.*
Ruth Keller et al., Antisense inhibition of the GDP–mannose pyrophosphorylase reduces the ascorbate content in transgenic plants leading to developmental changes during senescence, The Plant Journal (1999) 19(2), pp. 131–141.*

* cited by examiner

*Primary Examiner*—Amy J. Nelson
*Assistant Examiner*—Anne Kubelik
(74) *Attorney, Agent, or Firm*—Pioneer Hi-Bred International, Inc.; Kathryn K. Lappegard

(57) ABSTRACT

The invention relates to the genetic manipulation of plants, particularly to the expression of galactomannan biosynthetic genes in transformed plants. Nucleotide sequences for the GDP-mannose pyrophosphorylase genes and methods for their use are provided. The sequences find use in the production of gum in plants.

A nucleic acid encoding a GDP-mannose pyrophosphorylase from maize is taught, as are plants and plant cells transformed with it.

13 Claims, No Drawings

SEQUENCE LISTING

```
<160> NUMBER OF SEQ ID NOS: 2

<210> SEQ ID NO 1
<211> LENGTH: 1086
<212> TYPE: DNA
<213> ORGANISM: Zea mays
<220> FEATURE:
<223> OTHER INFORMATION: Nucleotide sequence for the maize GDP-mannose
      pyrophosphorylase gene

<400> SEQUENCE: 1
atgaaggccc tcattcttgt cgggggtttc ggaacccgcc ttcggccttt gactctgagc        60
ttcccgaaac ccctcgtgga ttttgcaaac aagcccatga ttctgcacca gatcgaagct       120
ttgaaagaag ttggggtcac agaggtggtt ttggctatca actatcgccc agaggtaatg       180
attaatttct tgaaggactt tgaggataag cttggcatca caattacatg ctcccaagag       240
actgagccct taggaaccgc tggccctctt gctctagcaa gggacaagct tgcggatgga       300
tctggccagc cattctttgt cctcaacagt gatgtcataa gcgaataccc atttgctgaa       360
ctcatcaaat ttcacaagtg tcatggtggt gaggcaacaa ttatggtcac taaggtggat       420
gaaccatcaa aatacggtgt tgtggttatg gaggaggcaa ctggcagggt ggaaaggttt       480
gttgagaagc caaaaatatt tgtgggtaac aagatcaatg ctgggattta cttactgaac       540
ccatctgtcc ttgaccgcat tgagctgagg ccaacatcaa ttgagaaaga ggtcttccct       600
caaattgcag ctgatcaaca gctctatgca atggtccttc caggtttttg gatggatgtt       660
ggtcagccta gggactacta tactggcttg cgtctttatc tagactcgat taggaagaaa       720
tcagctgcca agctagctac tggagcacat gttgttggca atgtgctggt gcatgagagc       780
```

```
gccaagattg agaaggttg tctgattggt cctgatgtcg ccattggacc tgggtgtgtt    840
gtggaggacg gcgtgaggct ttcccgctgc actgtcatgc gcggcgtgcg tatcaagaag    900
catgcttgca tctcaaacag cattatcggc tggcactcaa ctgttggtca atgggcacgg    960
atagagaata tgactatcct gggggaggat gttcatgtgt gtgatgaggt gtacagcaat   1020
ggcggtgttg ttctcccaca taaagagatc aagtcaagca ttctgaagcc tgagatcgtc   1080
atgtga                                                              1086
```

<210> SEQ ID NO 2
<211> LENGTH: 361
<212> TYPE: PRT
<213> ORGANISM: Zea mays
<220> FEATURE:
<223> OTHER INFORMATION: Amino acid sequence for the maize GDP-mannose
      pyrophosphorylase

<400> SEQUENCE: 2

```
Met Lys Ala Leu Ile Leu Val Gly Gly Phe Gly Thr Arg Leu Arg Pro
  1               5                  10                  15

Leu Thr Leu Ser Phe Pro Lys Pro Leu Val Asp Phe Ala Asn Lys Pro
             20                  25                  30

Met Ile Leu His Gln Ile Glu Ala Leu Lys Glu Val Gly Val Thr Glu
         35                  40                  45

Val Val Leu Ala Ile Asn Tyr Arg Pro Glu Val Met Ile Asn Phe Leu
     50                  55                  60

Lys Asp Phe Glu Asp Lys Leu Gly Ile Thr Ile Thr Cys Ser Gln Glu
 65                  70                  75                  80

Thr Glu Pro Leu Gly Thr Ala Gly Pro Leu Ala Leu Ala Arg Asp Lys
                 85                  90                  95

Leu Ala Asp Gly Ser Gly Gln Pro Phe Phe Val Leu Asn Ser Asp Val
            100                 105                 110

Ile Ser Glu Tyr Pro Phe Ala Glu Leu Ile Lys Phe His Lys Cys His
        115                 120                 125

Gly Gly Glu Ala Thr Ile Met Val Thr Lys Val Asp Glu Pro Ser Lys
    130                 135                 140

Tyr Gly Val Val Met Glu Glu Ala Thr Gly Arg Val Glu Arg Phe
145                 150                 155                 160

Val Glu Lys Pro Lys Ile Phe Val Gly Asn Lys Ile Asn Ala Gly Ile
                165                 170                 175

Tyr Leu Leu Asn Pro Ser Val Leu Asp Arg Ile Glu Leu Arg Pro Thr
            180                 185                 190

Ser Ile Glu Lys Glu Val Phe Pro Gln Ile Ala Ala Asp Gln Gln Leu
        195                 200                 205

Tyr Ala Met Val Leu Pro Gly Phe Trp Met Asp Val Gly Gln Pro Arg
    210                 215                 220

Asp Tyr Ile Thr Gly Leu Arg Leu Tyr Leu Asp Ser Ile Arg Lys Lys
225                 230                 235                 240

Ser Ala Ala Lys Leu Ala Thr Gly Ala His Val Gly Asn Val Leu
                245                 250                 255

Val His Glu Ser Ala Lys Ile Gly Glu Gly Cys Leu Ile Gly Pro Asp
            260                 265                 270

Val Ala Ile Gly Pro Gly Cys Val Val Glu Asp Gly Val Arg Leu Ser
        275                 280                 285

Arg Cys Thr Val Met Arg Gly Val Arg Ile Lys Lys His Ala Cys Ile
    290                 295                 300
```

```
Ser Asn Ser Ile Ile Gly Trp His Ser Thr Val Gly Gln Trp Ala Arg
305             310                 315                 320

Ile Glu Asn Met Thr Ile Leu Gly Glu Asp Val His Val Cys Asp Glu
            325                 330                 335

Val Tyr Ser Asn Gly Gly Val Val Leu Pro His Lys Glu Ile Lys Ser
            340                 345                 350

Ser Ile Leu Lys Pro Glu Ile Val Met
            355             360
```

MAIZE NUCLEIC ACID ENCODING A GDP-MANNOSE PYROPHOSPHORYLASE

CROSS-REFERENCE TO RELATED APPLICATIONS

This application claims priority to U.S. provisional application Ser. No. 60/096,782, filed Aug. 17, 1998, the contents of which are incorporated herein by reference.

FIELD OF THE INVENTION

The invention relates to the genetic manipulation of plants, particularly to the expression and regulation of GDP-mannose pyrophosphorylase in transformed plants.

BACKGROUND OF THE INVENTION

Gums are derived from the seeds of plants which accumulate certain polysaccharides as storage polymers. They are capable of forming gels or highly viscous solutions at low concentrations in solvents and have many industrial applications. Because gums can absorb large quantities of water, they are used as food additives to provide texture, prevent ice crystal formation, maintain crispness and retain moisture.

Gums also have uses outside of the food industry. For example, gums are used in the textile industry as dyeing and printing aids; in the petroleum industry as drilling agents for petroleum and gas wells; in the paper industry as binders and hardeners; in the mining industry for separation of minerals from crude ores; in the explosive industry to thicken explosive slurries and as desiccants; and in the cosmetic industry to thicken shampoos and conditioners. A new and rapidly emerging area for gum use is the pharmaceutical industry where gums have been reported to have applications as soluble fibers that lower cholesterol and blood pressure; as weight loss facilitators; as aids for the controlled release of drugs; in improving the microflora of the digestive system; in lowering blood glucose; and for prolonging the release of sugar during strenuous physical exercise.

Industrial gums are currently prepared from bacteria or from plant seeds. The main sources of seed-derived industrial gums are the subtropical plants Guar (*Cyamopsis tetragonoloba*), Locust Bean or carob (*Ceratonia siliqua*), Tara (*Caesalpina spinosa*), and Fenugreek (*Trigonella foenumgraecum*). More than 70% of natural plant gum is produced from Guar and Locust Bean.

Seed-derived gums are classified into two main categories: galactomannans and xyloglucans. Galactomannan, a linear polymer of mannosyl residues, substituted to varying degrees by galactosyl residues, is a major constituent of the seeds of the leguminous plants Guar, Fenugreek and Locust Bean. The differences in the properties of the galactomannan gums are determined by the mannose:galactose ratio in the polymer, which ranges from a low of 2 in Guar to a high of 4 in Locust Bean. Locust bean gum is considered to be of the highest quality for industrial applications and is the most expensive of all the plant seed gums.

Another class of plant gums, xyloglucans, has not received much attention, perhaps due to the very low yield of the source plants. Xyloglucans are the predominant storage polymers in the seeds of Nasturtium (*Tropaeoleum majus*), Tamarind (*Tamarindus indica*), and Balsam (*Impatiens balsamina*). Xyloglucan consists of a linear glucan backbone substituted with xylosyl residues. The xylosyl residues may be substituted with galactosyl residues.

Due to the high cost of gum derived from the seeds of subtropical plants, it is desirable to engineer transgenic plants which over-produce the gums galactomannan and/or xyloglucan. The present invention provides compositions and methods for the overexpression of enzymes and substrates required for the synthesis of the gum galactomannan.

SUMMARY OF THE INVENTION

The synthesis of the gum galactomannan is catalyzed by the enzymes mannan synthase and galactosyl transferase, from the substrates GDP-mannose and UDP-galactose (FIG. 1). The formation of the substrate GDP-mannose, from mannose-1-phosphate and GTP, is catalyzed by the enzyme GDP-mannose pyrophosphorylase. The present invention provides compositions and methods for manipulating the levels of enzymes in the galactomannan biosynthetic pathway in order to regulate gum production in plants, plant cells and plant tissues.

Protein glycosylation is required for cell growth. GDP-mannose is a substrate for glycosylation of proteins. Therefore, down-regulation of GDP-mannose pyrophosphorylase will result in decreased levels of GDP-mannose and concomitant decreases in protein glycosylation. Thus, by down-regulating GDP-mannose pyrophosphorylase, cell growth may be inhibited. The present invention includes antisense nucleic acids for GDP-mannose pyrophosphorylase which have use in decreasing GDP-mannose pyrophosphorylase and GDP-mannose levels. Also provided are expression cassettes encoding truncated GDP-mannose pyrophosphorylase for reduction of GDP-mannose pyrophosphorylase levels by cosuppression. Such methods and compositions inhibit cell growth, and are therefore useful in the production of dwarf plants, including ornamental Bonsai type plants.

Thus, it is an object of the invention to provide nucleotide sequences encoding GDP-mannose pyrophosphorylase gene and related genes. The sequences are useful in transforming plants for expression of GDP-mannose pyrophosphorylase or the antisense RNAs thereof Such sequences find use in regulating the levels of GDP-mannose, a substrate for the formation of the gum galactomannan and for protein glycosylation. Expression cassettes comprising GDP-mannose pyrophosphorylases and antisense RNAs thereto, are provided. Additionally provided are plants, plant cells, and plant tissues.

DETAILED DESCRIPTION OF THE INVENTION

The present invention discloses compositions and methods for the synthesis of the gum galactomannan in non-legume plants, plant cells and specific tissues, as well as for the increased expression in leguminous plants, plant cells and specific tissues. The methods involve modulation of the levels of enzymes in the galactomannan biosynthetic pathway. The synthesis of the gum galactomannan is catalyzed by the enzymes mannan synthase and galactosyl transferase, from the substrates GDP-mannose and UDP-galactose. The formation of the substrate GDP-mannose, from mannose-1-phosphate and GTP, is catalyzed by the enzyme GDP-mannose pyrophosphorylase.

The methods of the invention involve manipulating the pathway for gum production by over-expressing or up-regulating at least one enzyme in the biosynthetic pathway. By overexpression or up-regulation is meant causing an increase of 0.2–200 fold in the level of an RNA, enzyme or substrate in a transformed plant, as compared with the non-transformed plant. Preferably, the increase is 0.5–150 fold, and more preferably 1–100 fold. A key step in production of the gum galactomannan is providing an adequate supply of substrates, which include GDP-mannose and UDP-galactose. Thus, in particular the nucleotide sequence for maize GDP-mannose pyrophosphorylase is provided for use in priming gum production. It is recognized that if other enzymes in the galactomannan biosynthetic pathway are identified, they can be used to manipulate gum production or precursor accumulation in plants of interest.

Compositions also comprise antisense constructs for enzymes of the galactomannan biosynthetic pathway. Such compositions have use in down-regulating the levels of enzymes and/or substrates of the galactomannan biosynthetic pathway. When a plant carries a transgenic copy of an endogenous or foreign gene, both genes may be silenced. This phenomenon is termed cosuppression. Accordingly, constructs encoding are truncated enzymes of the GDP-mannose biosynthetic pathway, preferably encoding a truncated GDP-mannose pyrophosphorylase, are provided for use in cosuppression of the enzymes in the pathway. By down-regulation is meant causing a decrease of about 0.1–1000 fold, preferably about 1–500 fold, and more preferably about 5–100 fold, in a RNA, enzyme or substrate. In a preferred embodiment, compositions encoding antisense RNA to mRNA for GDP-mannose pyrophosphorylase are provided. Such compositions have use in decreasing levels of GDP-mannose, a substrate for protein glycosylation. The decrease in a substrate for protein glycosylation will result in the inhibition of cell growth or in cell death. By inhibiting cell growth, dwarf, miniature and bonsai plants may be produced.

The present invention is further drawn to compositions and methods for manipulating the levels of enzymes of the galactomannan biosynthetic pathway in plants, plant cells, and specific plant tissues. By enzymes of the galactomannan biosynthetic pathway is meant GDP-mannose pyrophosphorylase, mannan synthase and galactosyl transferase. It is recognized that as the galactomannan pathway is further elucidated, newly discovered galactomannan biosynthetic enzymes are included in the methods of the invention. Compositions are nucleic acids relating to genes encoding enzymes of the galactomannan biosynthetic pathway in plants, preferably to GDP-mannose pyrophosphorylase or GDP-mannose pyrophosphorylase-like genes. Preferably, the GDP-mannose pyrophosphorylase is native to maize or a leguminous plant. By native to maize or a leguminous plant is meant that the GDP-mannose pyrophosphorylase may be present in a naturally occurring or cultivated species of maize or a leguminous plant. Nucleotide sequences for a maize GDP-mannose pyrophosphorylase gene and the amino acid sequence for the GDP-mannose pyrophosphorylase protein encoded thereby are disclosed, as well as fragments and variants thereof. These sequences are set forth in SEQ ID NOS:1 and 2. The maize GDP-mannose pyrophorylase sequences were disclosed in U.S. provisional application Serial No. 60/096,782, filed Aug. 17, 1998, to which the instant application claims priority and which is incorporated herein by reference. The sequences find use in the construction of expression vectors for subsequent transformation into plants of interest, as probes for the isolation of other GDP-mannose pyrophosphorylase-like genes, as molecular markers, and the like.

By "fragment" is intended a portion of the nucleotide sequence or a portion of the amino acid sequence and hence protein encoded thereby. Fragments of a nucleotide sequence may encode protein fragments that retain the biological activity of the native GDP-mannose pyrophosphorylase protein. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the entire nucleotide sequence encoding the GDP-mannose pyrophosphorylase proteins of the invention.

Fragments of the invention include antisense sequences useful in decreasing expression of genes for enzymes of the galactomannan biosynthetic pathway, preferably of GDP-mannose pyrophosphorylase genes. Such antisense fragments may vary in length ranging from at least about 20 nucleotides, about 50 nucleotides, about 100 nucleotides, up to and including the entire coding sequence.

By "variants" is intended substantially similar sequences. The nucleotide sequences of the invention and the proteins encoded thereby include the native forms as well as variants thereof. For nucleotide sequences, conservative variants include those sequences that, because of the degeneracy of the genetic code, encode the amino acid sequences of galactomannan biosynthetic enzymes, preferably of a GDP-mannose pyrophosphorylase protein. Generally, nucleotide sequence variants of the invention will have 70%–99%, generally, 80%–98%, preferably 90–95% sequence identity to the native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. The variant proteins will be substantially homologous and functionally equivalent to the native proteins. A variant of a native protein is "substantially homologous" to the native protein when about 80%–99%, more preferably about 90%–99%, and most preferably about 95%–99% of its amino acid sequence is identical to the amino acid sequence of the native protein.

By "functionally equivalent" is intended that the sequence of the variant defines a chain that produces a protein having substantially the same biological effect as the native protein of interest. Thus, for purposes of the present invention, a functionally equivalent variant of GDP-mannose pyrophosphorylase will catalyze the formation of GDP-mannose from mannose-1-phosphate and GTP. Such functionally equivalent variants that comprise substantial sequence variations are also encompassed by the invention. The nucleotide sequences encoding the GDP-mannose pyrophosphorylase proteins of interest can be the naturally occurring sequence cloned from a plant GDP-mannose pyrophosphorylase gene, or they may be synthetically derived sequences. Such variants may result from, for example, genetic polymorphism or from human manipulation. Methods for such manipulations are generally known in the art. For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the GDP-mannose pyrophosphorylase protein of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

The genes of the galactomannan biosynthetic enzymes of the invention can be optimized for enhanced expression in plants of interest. See, for example, EPA0359472; WO91/16432; Perlak et al. (1991) *Proc. Natl. Acad. Sci. USA* 88:3324–3328; and Murray et al. (1989) *Nucleic Acids Res.* 17:477–498. In this manner, the genes can be synthesized utilizing plant-preferred codons. See, for example, Murray et al. (1989) *Nucleic Acids Res.* 17:477–498, the disclosure of which is incorporated herein by reference. In this manner, synthetic genes can also be made based on the distribution of codons a particular host uses for a particular amino acid. Thus, the nucleotide sequences can be optimized for expression in any plant. It is recognized that all or any part of the gene sequence may be optimized or synthetic. That is, synthetic or partially optimized sequences may also be used.

Alternatively, the sequences of the invention can be used to isolate corresponding sequences in other organisms, particularly other plants. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2d ed., Cold Spring Harbor Laboratory Press, Plainview, N.Y.) and Innis et al. (1990), PCR Protocols: A Guide to Methods and Applications (Academic Press, New York). Coding sequences isolated based on their sequence identity to the entire maize GDP-mannose pyrophosphorylase coding sequences set forth herein or to fragments thereof are encompassed by the present invention.

In a PCR method, nucleotide primers can be designed based on any 12 to 50 nucleotide stretch, preferably 12–30, nucleotide stretch of contiguous sequence. Pairs of primers can be used in PCR reactions for amplification of DNA sequences from cDNA or genomic DNA extracted from plants of interest. In addition, a single specific primer with a sequence corresponding to one of the nucleotide sequences disclosed herein can be paired with a primer having a sequence of the DNA vector in the cDNA or genomic libraries for PCR amplification of the sequences 5' or 3' to the nucleotide sequences disclosed herein. Similarly, nested primers may be used instead of a single specific primer for the purposes of the invention. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Ignis et al., eds. (1990) *PCR Protocols: A Guide to Methods and Applications* (Academic Press, New York).

In a hybridization method, the hybridization probes may be genomic DNA fragments, cDNA fragments, RNA fragments, or other oligonucleotides, and may be labeled with a detectable group such as 32P, or any other detectable marker. Probes for hybridization can be made by labeling synthetic oligonucleotides based on the maize GDP-mannose pyrophosphorylase nucleotide sequences of the invention. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), hereby incorporated by reference. The labeled probes can be used to screen cDNA or genomic libraries made from plants of interest. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

In hybridization techniques, all or part of the known coding sequence is used as a probe that selectively hybridizes to other possible GDP-mannose pyrophosphorylase coding sequences present in a population of cloned genomic DNA fragments or cDNA fragments (i.e., genomic or cDNA libraries) from a chosen organism. To achieve specific hybridization under a variety of conditions, such probes include sequences that are unique and are preferably at least about 10 nucleotides in length, and most preferably at least about 20 nucleotides in length. Such probes may be used to amplify corresponding GDP-mannose pyrophosphorylase coding sequences from a chosen organism by PCR. This technique may be used to isolate other possible GDP-mannose pyrophosphorylase coding sequences from a desired organism or as a diagnostic assay to determine the presence of a GDP-mannose pyrophosphorylase coding sequence in an organism. Hybridization techniques include hybridization screening of plated DNA libraries (either plaques or colonies; see, e.g., Innis et al., eds. (1990) *PCR Protocols: A Guide to Methods and Applications* (Academic Press, New York)).

The isolated DNA sequences further comprise DNA sequences isolated from other plants by hybridization with partial sequences obtained from the maize GDP-mannose pyrophosphorylase sequences of the invention. Conditions that will permit other DNA sequences to hybridize to the DNA sequences disclosed herein can be determined in accordance with techniques generally known in the art. For example, hybridization of such sequences may be carried out under conditions of reduced stringency, medium stringency, or high stringency conditions.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization an/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions may also be achieved with the addition of destabilizing agents such as formamide. By "low stringency conditions" is meant hybridization with a buffer solution of 30% formamide, 1 M NaCl, 1% SDS(sodium dodecyl sulphate) at 37° C., and a wash in 2×SSC (20× SSC=3.0 M NaCl/0.3 M trisodium citrate) at 50° C. By "moderate stringency conditions" is meant hybridization in 40% formamide, 1 M NaCl, 1% SDS at 37° C., and a wash in 1×SSC at 60° C. By "high stringency conditions" is meant hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem* 138:267–284 91984): $T_m$=81.5° C.+16.6 (log M)+0.41 (%GC)–0.61 (% form)–500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequence with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

In general, sequences that confer GDP-mannose pyrophosphorylase activity and hybridize to the reference DNA sequences disclosed herein will have at least 70%, at least 75%, at least 80%, at least 85%, at least 90% and most preferably about 95–100% sequence identity to the reference GDP-mannose pyrophosphorylase sequences of the present invention.

Methods of alignment of sequences for comparison are well-known in the art. For example, optimal alignment of sequences for comparison may be conducted by the local homology algorithm of Smith and Waterman (1981) *Adv. Appl. Math.* 2:482; by the homology alignment algorithm of Needleman and Wunsch (1970) *J. Mol. Biol.* 48:443; and by the search for similarity method of Pearson and Lipman (1988) *Proc. Natl. Acad. Sci.* 85:2444. For the purposes of the instant invention, sequence identity is determined by the GAP program, version 10 in the Wisconsin Genetics Software Package, Genetics Computer Groups (GCG) (575 Science Drive, Madison, Wis.) using the default settings. See, Ausubel et al., eds. (1995) *Current Protocols in Molecular Biology*, Chapter 19 (Greene Publishing and Wiley-Interscience, New York).

The sequences of the invention are useful to transform plants and manipulate the levels of the enzymes of the galactomannan biosynthetic pathway, preferably of GDP-mannose pyrophosphorylase in the transformed plant. Such manipulation provides the ability to up-regulate or down-regulate the production of the gum galactomannan and/or of substrates in the galactomannan biosynthetic pathway such as GDP-mannose. Toward this end, the sequences of the invention may be utilized in expression cassettes with either constitutive or tissue-specific promoters.

Constitutive promoters would provide a constant supply of one or more enzymes of the galactomannan biosynthetic pathway throughout the plant. Alternatively, a constitutive promoter driving the expression of antisense RNA to an mRNA of the galactomman biosynthetic pathway would result in a decrease in an enzyme of the galactomannan pathway, and a concomitant decrease in gum production. Furthermore, constitutive expression of an antisense RNA to a GDP-mannose pyrophosphorylase mRNA would result in a decrease in GDP-mannose, a precursor of protein glycosylation, inhibit cell growth or cause cell death. Such constitutive promoters include, for example, the core promoter of the Rsyn7 (copending U.S. patent application Ser. No. 08/661,601); the promoter for the small subunit of ribulose-1,5-bis-phosphate carboxylase; promoters from tumor-inducing plasmids of *Agrobacterium tumefaciens*; such as the nopaline synthase and octopine synthase promoters; and viral promoters such as the cauliflower mosaic virus (CaMV) 19S and 35S promoters; the figwort mosaic virus 35S promoter, the rice actin promoter (McElroy et al. (1990) *Plant Cell* 2:163–171); the ubiquitin promoter (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); the MAS promoter (Velten et al (1984) *EMBO J.* 3:2723–2730); the ALS promoter (U.S. patent application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142. For beans, Scp1 is a preferred constitutive promoter.

Alternatively, it may be desired to express an enzyme of the galactomannon biosynthetic pathway in a tissue-specific manner. Thus tissue-specific promoters, particularly seed-preferred promoters may be used. Examples of tissue-specific promoters include seed-preferred, leaf-specific, and tassel-specific promoters. Seed-preferred promoters include both seed-specific promoters (those promoters active during seed development such as promoters of seed storage proteins) as well as seed-germinating promoters (those promoters active during seed germination). See Thompson et at, (1 989) *BioEssays* 10: 108, incorporated herein in its entirety by reference. Such seed-preferred promoters include, but are not limited to, Cim1 (cytokinin-induced message); cZ19B1 (maize 19KDa zein); and celA (cellulose synthase). Gama-zein is a preferred endosperm-specific promoter. Glob-1 is a preferred embryo-specific promoter. For dicots, seed-specific promoters include, but are not limited to, bean b-phaseolin, napin, β-conglycinin, soybean lectin, and the like. For monocots, seed-specific promoters include, but are not limited to, maize 15 kD zein, 22 kD zein, 27 kD zein, g-zein, waxy, shrunken 1, shrunken 2, globulin 1, etc. Leaf-specific promoters include, Yamamoto et al. (1997) *Plant J.* 12(2):255–265; Kawamata et a. (1997) *Plant Cell Physiol.* 38(7):792–803; Hansen et at (1997) *Mol. Gen. Genet.* 254(3):337–343; Russell et al (1997) *Transgenic Res.* 6(2):157–168; Rinehart et al (1996) *Plant Physiol.* 112(3): 1331–1341; Van Camp et al. (1996) *Plant Physiol.* 112(2): 525–535; Canevascini et al. (1996) *Plant Physiol.* 112(2): 513–524; Yamamoto et al. (1994) *Plant Cell Physiol.* 35(5): 773–778; Lam (1994) *Results Probl. Cell Differ.* 20:181–196; Orozco et al. (1993) *Plant Mol. Biol.* 23(6): 1129–1138; Matsuoka et al. (1993) *Proc. Natl. Acad. Sci. USA* 90(20):9586–9590; and Guevara-Garcia et al (1993) *Plant J.* 4(3):495–505. However, other promoters useful in the practice of the invention are known to those of skill in the art.

Tissue-specific promoters may also be use to express antisense RNAs to mRNAs of the galactomannan biosynthetic pathway. In one embodiment, a tissue-specific and inducible promoter is used to drive expression of an antisense RNA to a GDP-mannose pyrophosphorylase mRNA. Induction of the anti-sense RNA in a specific tissue to result in the inhibition of growth of that tissue. Such induction would be useful to inhibit the growth of a plant tissue after it has performed its function, yet continues to draw on the energy resources of the plant for its maintenance. An example of this tissue type is corn tassel.

The sequences of the invention may be used in expression cassettes for expression in any plant of interest. Where expression cassettes are needed, such expression cassettes will comprise a transcriptional initiation region linked to the coding sequence or antisense sequence of the nucleotide of interest. Such an expression cassette is provided with a plurality of restriction sites for insertion of the sequence to be under the transcriptional regulation of the regulatory regions. The expression cassette may additionally contain selectable marker genes.

The transcriptional initiation region, the promoter, may be native or analogous or foreign or heterologous to the plant host. By foreign is intended that the transcriptional initiation region is not found in the native plant into which the transcriptional initiation region is introduced. As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention. Additionally, the promoter may be the natural sequence or alternatively a synthetic sequence. As used herein a chimeric gene comprises a coding sequence operably linked to a transcription initiation region that is heterologous to the coding sequence.

The transcriptional cassette will include in the 5'-to-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91: 151–158; Ballas et al. (1989) *Nucleic Acids Res.* 17:7891–7903; Joshi et al. (1987) *Nucleic Acids Res.* 15:9627–9639.

Nucleotide sequences of the invention are provided in expression cassettes for expression in the plant of interest. The cassette will include 5' and 3' regulatory sequences operably linked to the sequence of interest. The cassette may additionally contain at least one additional sequence to be co-transformed into the organism. Alternatively, the additional sequence(s) can be provided on another expression cassette.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The sequences of the present invention can be used to transform or transfect any plant. In this manner, genetically modified plants, plant cells, plant tissue, seed, and the like can be obtained. Plants of particular interest include grain plants which provide seeds of interest, oil seed plants and leguminous plants. Seeds of interest include grain seeds, such as corn, wheat, barley, rice, sorghum, rye, etc. Oil seed plants include cotton, soybean, safflower, sunflower, Brassica, alfalfa, etc. Leguminous plants include beans and peas. Beans include guar, locust bean, fenugreek, soybean, garden beans, cowpea, mungbean, lima bean, fava bean, lentils, chickpea, etc.

Transformation protocols as well as protocols for introducing nucleotide sequences into plants may vary depending on the type of plant or plant cell, i.e. monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (U.S. Pat. No. 5,563,055), direct gene transfer (Paszkowski et al. (1984) *EMBO J.* 3:2717–2722), and ballistic particle acceleration (see, for example, Sanford et al, U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) In *Vitro Cell Dev. Biol.* 27P: 175–182 (soybean); Singh et al. (1998) *Theor. Appl. Genet.* 96:319–324 (soybean); Datta et al. ( 1990) *Biotechnology* 8:736–740 (rice); Klein et al. (1988) *Proc. Natl. Acad. Sci. USA*

85:4305–4309 (maize); Klein et al. (1988) *Biotechnology* 6:559–563 (maize); Klein et al. (1988) *Plant Physiol.* 91:440–444 (maize); Fromm et al. (1990) *Biotechnology* 8:833–839 (maize); Hooydaas-Van Slogteren and Hooykaas (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

Plant cells expressing GDP-mannose pyrophosphorylase may be detected by a variety of methods known to those skilled in the art. See, for example, Szumilo et al., (1993) *J. Biol. Chem.* 268:17943–17950, the contents of which are incorporated by reference. Such assays include Northern assays for the detection of GDP-mannose pyrophosphorylase mRNA (See Sambrook et al. (1989) A Laboratory Manual (2d ed., Cold Spring Harbor Laboratory Press, Plainview, N.Y.)); enzymatic assays for GDP-mannose pyrophosphorylase activity and assays for levels of GDP-mannose.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The following examples are offered by way of illustration and not by way of limitation.

EXPERIMENTAL

Example 1

Incorporation of GDP-Mannose Pyrophosphorylase DNA Sequences into Expression Vectors A full-length cDNA sequence encoding maize GDP-mannose pyrophosphorylase gene was isolated from the maize genomic project. Maize root and culture cell cDNA libraries were constructed according to the manufacturer's instructions (Gibco-BRL). cDNA clones were partially sequenced from 5-end. 5-sequences of cDNA clones were then compared to the *Saccharomyces cerevisiae* V1 G9 GDP-mannose pyrophosphorylase gene (Hashimoto et al., (1997) J. Biol. Chem. 272:16308–16314) with the BlastX subroutine. A clone that showed significant homology to the gene was sequenced completely. The nucleotide sequence and the deduced amino acid sequence are set forth in SEQ ID NOS:1 and 2, respectively. Gene sequences are cloned into a plasmid vector in the sense orientation so that they are under the transcriptional control of the ubiquitin promoter. A selectable marker gene may reside on this plasmid or may be introduced as part of a second plasmid. The transformation construct is then available for introduction into maize embryos by bombardment methods as described in Example 2.

Example 2

Transformation and Regeneration of Maize Callus

Immature maize embryos from greenhouse donor plants are bombarded with a plasmid containing the GDP-mannose pyrophosphorylase gene of the invention operably linked to the ubiquitin promoter plus a plasmid containing the selectable marker gene PAT (Wohlleben et al. (1988) *Gene* 70:25–37) that confers resistance to the herbicide Bialophos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate. These are cultured on 560 L medium for 4 days prior to bombardment, in the dark. The day of bombardment, the embryos are transferred to 560 Y medium for 4 hours, arranged within the 2.5-cm target zone.

Preparation of DNA

A plasmid vector comprising the GDP-mannose pyrophosphorylase gene of the invention operably linked to the ubiquitin promoter is constructed. This plasmid DNA plus plasmid DNA containing a PAT selectable marker is precipitated onto 1.1 $\mu$m (average diameter) tungsten pellets using a $CaCl_2$ precipitation procedure as follows:

100 $\mu$l prepared tungsten particles in water

10 $\mu$l (1 $\mu$g) DNA in TrisEDTA buffer (1 $\mu$g total)

100 $\mu$l 2.5 M $CaCl_2$

10 $\mu$l 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry about 2 minutes before bombardment.

Particle Gun Treatment

The sample plates are bombarded at level #4 in particle gum #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialophos, and subcultured every 2 weeks. After approximately 10 weeks of selection, selection-resistant callus clones are sampled for PCR and activity of the GDP-mannose pyrophosphorylase gene of interest. Positive cultures are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored for expression of the GDP-mannose pyrophosphorylase gene of interest.

| Ingredient | Amount | Unit |
|---|---|---|
| D-I $H_2O$ | 900 | ml |
| CHU (N6) Basal Salts (SIGMA C-1416) | 1.600 | g |
| N6 Macronutrients 10X Stock ## | 60 | ml |
| Potassium Nitrate | 1.680 | g |
| B5H Minor Salts 1000X ### | 0.6 | ml |
| B5H Fe Na EDTA 100X #### | 6.0 | ml |
| Eriksson's Vitamin Mix (1000X SIGMA-1511) | 0.4 | ml |
| S & H Vitamin Mixture 100X Stock (S3766) | 6.0 | ml |
| Thiamine.HCL 0.4 mg/ml | 0.5 | ml |
| L-Proline | 1.980 | g |
| Casein Hydrolystate (acid) | 0.300 | g |
| Sucrose | 20.000 | g |
| Glucose | 0.600 | g |
| 2,4-D 0.5 mg/ml | 1.6 | ml |
| Gelrite @ | 2.000 | g |
| Dicamba 1 mg/ml # | 1.2 | ml |
| Silver Nitrate 2 mg/ml # | 1.7 | ml |

Directions:
@=Add after bringing up to volume
=Add after sterilizing and cooling to temp.
Dissolve ingredients in polished D-I $H_2O$ in sequence
Adjust to pH 5.8
Bring up to volume with polished D-I $H_2O$ after adjusting pH
Sterilize and cool to 60° C.
.##=Dissolve 1.660 g of Calcium Chloride Dihydrate in 950 ml of polished D-I $H_2O$.
Then dissolve 4.629 of Ammonium Sulfate; 4.000 g of Potassium Phosphate Monobasic $KH_2PO_4$; 1.850 g of Magnesium Sulfate 7-$H_2O$, $MgSO_4$, 7$H_2O$; and 28.300 g of Potassium Nitrate into sequence. Bring up to volume with polished D-I $H_2O$.
=Dissolve 3.000 g of Boric Acid; 10.000 g of Manganous Sulfate Monohydrate; 0.250 g of Sodium Molybdate Dihydrate; and 0.750 g of Potassium Iodide in polished D-I $H_2O$ in sequence. Bring up to volume with polished D-I $H_2O$.
=Dissolve 3.700 g of Disodium EDTA Dihydrate and 2.790 g of Ferrous Sulfate 7-Hydrate into D-I $H_2O$. Bring up to volume with D-I $H_2O$.
Total Volume (L)=1

| Ingredient | Amount | Unit |
|---|---|---|
| D-I $H_2O$ | 900 | ml |
| CHU (N6) Basal Salts (SIGMA C-1416) | 1.600 | g |
| N6 Macronutrients 10X Stock ## | 60 | ml |
| Potassium Nitrate | 1.680 | g |
| B5H Minor Salts 1000X ### | 0.6 | ml |
| B5H Fe Na EDTA 100X #### | 6.0 | ml |
| Eriksson's Vitamin Mix (1000X SIGMA-1511) | 0.4 | ml |
| S & H Vitamin Mixture 100X Stock (S3766) | 6.0 | ml |
| Thiamine.HCL 0.4 mg/ml | 0.5 | ml |
| L-Proline | 1.980 | g |
| Casein Hydrolysate (acid) | 0.300 | g |
| Sucrose | 20.000 | g |
| Glucose | 0.600 | g |
| 2, 4-D 0.5 mg/ml | 1.6 | ml |
| Gelrite @ | 2.000 | g |
| Dicamba 1 mg/ml # | 1.2 | ml |
| Silver Nitrate 2 mg/ml # | 1.7 | ml |
| Bialaphos 1 mg/ml # | 3.0 | ml |

Directions:
@=Add after bringing up to volume
=Add after sterilizing and cooling to temp.
Dissolve ingredients in polished D-I $H_2O$ in sequence
Adjust to pH 5.8
Bring up to volume with polished D-I $H_2O$ after adjusting pH
Sterilize and cool to 60° C.
=Dissolve 1.660 g of Calcium Chloride Dihydrate in 950 ml of polished D-I $H_2O$. Then dissolve 4.629 of Ammonium Sulfate; 4.000 g of Potassium Phosphate Monobasic $KH_2PO_4$; 1.850 g of Magnesium Sulfate 7-$H_2O$, $MgSO_4$, 7$H_2O$; and 28.300 g of Potassium Nitrate into sequence. Bring up to volume with polished D-I $H_2O$.
=Dissolve 3.000 g of Boric Acid; 10.000 g of Manganous Sulfate Monohydrate; 0.250 g of Sodium Molybdate Dihydrate; and 0.750 g of Potassium Iodide in polished D-I $H_2O$ in sequence. Bring up to volume with polished D-I $H_2O$.
=Dissolve 3.700 g of Disodium EDTA Dihydrate and 2.790 g of Ferrous Sulfate 7-Hydrate into D-I $H_2O$. Bring up to volume with D-I $H_2O$.
Total Volume (L)=1

| Ingredient | Amount | Unit |
|---|---|---|
| D-I $H_2O$ | 900 | ml |
| CHU (N6) Basal Salts (SIGMA C-1416) | 1.600 | g |
| N6 Macronutrients 10X Stock ## | 60 | ml |
| Potassium Nitrate | 1.680 | g |
| B5H Minor Salts 1000X ### | 0.6 | ml |
| B5H Fe Na EDTA 100X #### | 6.0 | ml |
| Eriksson's Vitamin Mix (1000X SIGMA-1511) | 0.4 | ml |
| S & H Vitamin Mixture 100X Stock (S3766) | 6.0 | ml |
| Thiamine.HCL 0.4 mg/ml | 0.5 | ml |
| Sucrose | 20.000 | g |
| Glucose | 0.600 | g |
| 2, 4-D 0.5 mg/ml | 1.6 | ml |
| Gelrite @ | 2.000 | g |
| Dicamba 1 mg/ml # | 1.2 | ml |
| Silver Nitrate 2 mg/ml # | 0.425 | ml |
| Bialaphos 1 mg/ml # | 3.0 | ml |

Directions:
@=Add after bringing up to volume
=Add after sterilizing and cooling to temp.
Dissolve ingredients in polished D-I $H_2O$ in sequence
Adjust to pH 5.8
Bring up to volume with polished D-I $H_2O$ after adjusting pH
Sterilize and cool to 60° C.##=Dissolve 1.660 g of Calcium Chloride Dihydrate in 950 ml of polished D-I $H_2O$. Then dissolve 4.629 of Ammonium Sulfate; 4.000 g of Potassium Phosphate Monobasic $KH_2PO_4$; 1.850 g of Magnesium Sulfate 7-$H_2O$, $MgSO_4$, 7$H_2O$; and 28.300 g of Potassium Nitrate into sequence. Bring up to volume with polished D-I $H_2O$.
=Dissolve 3.000 g of Boric Acid; 10.000 g of Manganous Sulfate Monohydrate; 0.250 g of Sodium Molybdate Dihydrate; and 0.750 g of Potassium Iodide in polished D-I H$_2$O in sequence. Bring up to volume with polished D-I H$_2$O.

=Dissolve 3.700 g of Disodium EDTA Dihydrate and 2.790 g of Ferrous Sulfate 7-Hydrate into D-I H$_2$O. Bring up to volume with D-I H$_2$O.

Total Volume (L)=1

| Ingredient | Amount | Unit |
|---|---|---|
| D-I H$_2$O | 800 | ml |
| CHU (N6) Basal Salts (SIGMA C-1416) | 1.600 | g |
| N6 Macronutrients 10X Stock ## | 60 | ml |
| Potassium Nitrate | 1.680 | g |
| B5H Minor Salts 1000X ### | 0.6 | ml |
| B5H Fe Na EDTA 100X #### | 6.0 | ml |
| Eriksson's Vitamin Mix (1000X SIGMA-1511) | 0.4 | ml |
| S & H Vitamin Mixture 100X Stock (S3766) | 6.0 | ml |
| Thiamine.HCL 0.4 mg/ml | 0.5 | ml |
| L-Proline | 1.980 | g |
| Casein Hydrolysate (acid) | 0.300 | g |
| Sucrose | 120.000 | g |
| Glucose | 0.600 | g |
| 2, 4-D 0.5 mg/ml | 1.6 | ml |
| Gelrite @ | 2.000 | g |
| Dicamba 1 mg/ml # | 1.2 | ml |
| Silver Nitrate 2 mg/ml # | 1.7 | ml |

Directions:
@=Add after bringing up to volume
=Add after sterilizing and cooling to temp.
Dissolve ingredients in polished D-I H$_2$O in sequence
Adjust to pH 5.8
Bring up to volume with polished D-I H$_2$O after adjusting pH
Sterilize and cool to 60° C.

=Dissolve 1.660 g of Calcium Chloride Dihydrate in 950 ml of polished D-I H$_2$O. Then dissolve 4.629 of Ammonium Sulfate; 4.000 g of Potassium Phosphate Monobasic KH$_2$PO$_4$; 1.850 g of Magnesium Sulfate 7-H$_2$O, MgSO$_4$, 7H$_2$O; and 28.300 g of Potassium Nitrate into sequence. Bring up to volume with polished D-I H$_2$O.

=Dissolve 3.000 g of Boric Acid; 10.000 g of Manganous Sulfate Monohydrate; 0.250 g of Sodium Molybdate Dihydrate; and 0.750 g of Potassium Iodide in 950 ml of polished D-I H$_2$O in sequence. Bring up to volume with polished D-I H$_2$O.####=Dissolve 3.700 g of Disodium EDTA Dihydrate and 2.790 g of Ferrous Sulfate 7-Hydrate into 950 ml of D-I H$_2$O. Bring up to volume with D-I H$_2$O.

Total Volume (L)=1

| Ingredient | Amount | Unit |
|---|---|---|
| D-I H$_2$O | 950 | ml |
| MS Salts (GIBCO 11117-074) | 4.300 | g |
| Myo-Inositol | 0.100 | g |
| MS Vitamins Stock Solution ## | 5.0 | ml |
| Sucrose | 40.000 | g |
| Bacto-Agar @ | 6.000 | g |

Directions:
@=Add after bringing up to volume
Dissolve ingredients in polished D-I H$_2$O in sequence
Adjust to pH 5.6
Bring up to volume with polished D-I H$_2$O after adjusting pH
Sterilize and cool to 60° C.

=Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Desiccator. Store for one month, unless contamination or precipitation occur, then make fresh stock.

Total Volume (L)=1

| Ingredient | Amount | Unit |
|---|---|---|
| D-I H$_2$O | 950 | ml |
| MS Salts | 4.300 | g |
| Myo-Inositol | 0.100 | g |
| MS Vitamins Stock Solution ## | 5.0 | ml |
| Zeatin .5 mg/ml | 1.0 | ml |
| Sucrose | 60.000 | g |
| Gelrite @ | 3.000 | g |
| Indole Acetic Acid 0.5 mg/ml # | 2.0 | ml |
| .1 mM Absissic Acid | 1.0 | ml |
| Bialaphos 1 mg/ml # | 3.0 | ml |

Directions:
@=Add after bringing up to volume
Dissolve ingredients in polished D-I H$_2$O in sequence
Adjust to pH 5.6
Bring up to volume with polished D-I H$_2$O after adjusting pH
Sterilize and cool to 60° C.
Add 3.5 g/L of Gelrite for cell biology.

=Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Desiccator. Store for one month, unless contamination or precipitation occur, then make fresh stock.

Total Volume (L)=1

| Ingredient | Amount | Unit |
|---|---|---|
| D-I Water, Filtered | 950 | ml |
| CHU (N6) Basal Salts (SIGMA C-1416) | 4.000 | g |
| Eriksson's Vitamin Mix (1000X SIGMA-1511 | 0.4 | ml |
| Thiamine.HCL 0.4 mg/ml | 1.25 | ml |
| Sucrose | 20.000 | g |
| 2, 4-D 0.5 mg/ml | 2.0 | ml |
| L-Proline | 2.880 | g |
| Gelrite @ | 2.000 | g |
| Silver Nitrate 2 mg/ml # | 4.25 | ml |

Directions:
@=Add after bringing up to volume
=Add after sterilizing and cooling to temp.
Dissolve ingredients in D-I H$_2$O in sequence
Adjust to pH 5.8 with KOH
Bring up to volume with D-I H$_2$O
Sterilize and cool to room temp.
Total Volume (L)=1

| Ingredient | Amount | Unit |
|---|---|---|
| D-I Water, Filtered | 950 | ml |
| CHU (N6) Basal Salts (SIGMA C-1416) | 4.000 | g |
| Eriksson's Vitamin Mix (1000X SIGMA-1511 | 1.0 | ml |

-continued

| Ingredient | Amount | Unit |
|---|---|---|
| Thiamine.HCL 0.4 mg/ml | 1.25 | ml |
| Sucrose | 30.000 | g |
| 2, 4-D 0.5 mg/ml | 4.0 | ml |
| Gelrite @ | 3.000 | g |
| Silver Nitrate 2 mg/ml # | 0.425 | ml |
| Bialaphos 1 mg/ml # | 3.0 | ml |

Directions:
@=Add after bringing up to volume
=Add after sterilizing and cooling to temp.
Dissolve ingredients in D-I H₂O in sequence
Adjust to pH 5.8 with KOH
Bring up to volume with D-I H₂O
Sterilize and cool to room temp.
Total Volume (L)=1

| Ingredient | Amount | Unit |
|---|---|---|
| D-1 Water, Filtered | 950 | ml |
| CHU (N6) Basal Salts (SIGMA C-1416) | 4.000 | g |
| Eriksson's Vitamin Mix (1000X SIGMA-1511 | 1.0 | ml |
| Thiamine.HCL 0.4 mg/ml | 1.25 | ml |
| Sucrose | 120.000 | g |
| 2,4-D 0.5 mg/ml | 2.0 | ml |
| L-Proline | 2.880 | g |
| Gelrite @ | 2.000 | g |
| Silver Nitrate 2 mg/ml # | 4.25 | ml |

Directions:
@=Add after bringing up to volume
=Add after sterilizing and cooling to temp.
Dissolve ingredients in D-I H₂O in sequence
Adjust to pH 5.8 with KOH
Bring up to volume with D-I H₂O
Sterilize and cool to room temp.
Autoclave less time because of increased sucrose
Total Volume (L)=1

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleotide sequence selected from the group consisting of:
   a) a nucleotide sequence encoding the amino acid sequence of SEQ ID NO:2 and;
   b) the nucleotide sequence set forth in SEQ ID NO:1.

2. The isolated nucleotide sequence of claim 1, wherein the nucleotide sequence is set forth in SEQ ID NO:1.

3. An isolated nucleotide sequence that encodes the amino acid sequence of SEQ ID NO:2.

4. An expression cassette comprising the nucleotide sequence of claim 1, wherein said nucleotide sequence is operably linked to a promoter that drives expression in a plant.

5. The expression cassette of claim 4, wherein said promoter is a tissue-specific promoter.

6. The expression cassette of claim 5, wherein said promoter is a seed-preferred promoter.

7. The expression cassette of claim 4, wherein said promoter is a constitutive promoter.

8. A recombinant plant cell having stably incorporated into its genome at least one nucleotide sequence of claim 1; wherein said nucleotide sequence is operably linked to a promoter that drives expression in a plant.

9. A transformed plant having stably incorporated into its genome at least one nucleotide sequence of claim 1, wherein said sequence is operably linked to a promoter that drives expression in a plant.

10. The plant of claim 9, wherein said plant is a monocot.

11. The plant of claim 9, wherein said plant is maize, wheat, rice, barley, sorghum, or rye.

12. The plant of claim 9, wherein said plant is a dicot.

13. The plant of claim 9, wherein said plant is soybean, Brassica, sunflower, alfalfa, or safflower.

* * * * *

UNITED STATES PATENT AND TRADEMARK OFFICE
CERTIFICATE OF CORRECTION

PATENT NO. : 6,706,951 B1
DATED : March 16, 2004
INVENTOR(S) : Kanwarpal S. Dhugga It is certified that error appears in the above-identified patent and that said Letters Patent is hereby corrected as shown below:

Title page,
Item [75], Inventors, should read as follows:
-- [75]   Inventors:      Kanwarpal S. Dhugga, Johnston, IA (US) --
Item [57], ABSTRACT,
Line 7, should read -- A nucleic acid encoding a GDP-mannose pyrophosphorylase from maize is taught, as are plants and plant cells transformed with it. --

Signed and Sealed this

Twenty-third Day of November, 2004

JON W. DUDAS
*Director of the United States Patent and Trademark Office*